United States Patent [19]

Choyce

[11] 4,315,337
[45] Feb. 16, 1982

[54] AUTOCLAVABLE ANTERIOR CHAMBER IMPLANT

[76] Inventor: David P. Choyce, 9 Drake Rd., Westcliffe-on-Sea, Essex SSO 8LR, England

[21] Appl. No.: 171,889

[22] Filed: Jul. 24, 1980

[30] Foreign Application Priority Data

Jul. 26, 1979 [GB] United Kingdom ............... 26094/79
Mar. 25, 1980 [GB] United Kingdom ............... 10045/80

[51] Int. Cl.³ ........................ A61F 1/16; A61F 1/24
[52] U.S. Cl. ................................................. 3/13
[58] Field of Search ............................... 3/13, 1

[56] References Cited

U.S. PATENT DOCUMENTS

| | | | |
|---|---|---|---|
| 3,480,971 | 12/1969 | Smith | 3/13 |
| 3,711,870 | 1/1973 | Deitrick | 3/13 |
| 4,028,082 | 6/1977 | Krohn et al. | 3/13 |
| 4,073,014 | 2/1978 | Poler | 3/13 |
| 4,080,709 | 3/1978 | Poler | 3/13 |
| 4,122,556 | 10/1978 | Poler | 3/13 |
| 4,164,794 | 8/1979 | Spector et al. | 3/1 X |
| 4,249,271 | 2/1981 | Poler | 3/13 |

OTHER PUBLICATIONS

"The Choyce Mark VIII and Mark IX Anterior Chamber Implants", by D. P. Choyce, Am. Intr-Ocular Implant Soc. J., vol. V, Jul. 1979, (Presented at the U.S. Intraocular Lens Symposium in Los Angeles, Apr. 1979), pp. 217-221.

The Rayner Choyce Mark VIII Anterior Chamber Implant, Rayner & Keeler Limited, Catalogue No. 469, (3 pages).

*Primary Examiner*—Ronald L. Frinks
*Attorney, Agent, or Firm*—Lewis Messulam

[57] ABSTRACT

The invention relates to anterior chamber implants of the type having a haptic with feet resting on the anterior surface of the iris. To enable the implant to be autoclaved, the optic is made of glass and the haptic is separately formed from an autoclavable inert material. Titanium and a polyethersulphone thermoplastic material are disclosed as suitable materials for the haptic.

1 Claim, 3 Drawing Figures

AUTOCLAVABLE ANTERIOR CHAMBER IMPLANT

The present invention relates to an anterior chamber implant.

Intraocular implants have been developed over the last twenty-five years and are used for the correction of aphakia. The implant, which is intended to be inserted within the eye, has a lens aligned with the pupil to act instead of the natural lens and held in place by a haptic, various forms of which have been proposed in the past and which have met in practice with varying degrees of success.

There have been proposals for placing the lens in the anterior chamber, that is to say between the iris and the cornea, in the iris plane and behind the iris in the posterior chamber.

In respect of iris plane and posterior chamber implants, the lens blocks the aperture of the pupil and impedes natural circulation of fluid within the eye. This can give rise to various complications and is one of the reasons why such lenses have not had any degree of success.

Anterior chamber implants, on the other hand, have been developed to a point beyond mere experimentation and are now in extensive use. Examples of anterior chamber implants which have proved successful are the Choyce Mark VIII and Mark IX implants which have been developed in co-operation with the present inventor.

The haptic portions of the Mark VIII and the Mark IX implants mentioned above comprise two pairs of feet which extend from diametrically opposite sides of the lens which rest on a peripheral portion of the iris. The feet are substantially flat and rest in the same plane as one another, the lens being arranged in a plane spaced from the plane of the feet so as to stand sufficiently clear from the pupil to permit natural circulation of fluid within the anterior chamber.

Other forms of haptic have also been proposed and in particular one proposal has been the so-called iris clip. In this case, wires anchored in the periphery of the lens clip in front of and behind the iris to retain the lens in place. This technique has been used both for anterior chamber implants, iris plane implants and posterior chamber implants. In some cases, the clip is made resilient to allow the iris to open and close while continuing to hold the lens in position. It is believed, however, that none of these iris clip lenses has been successfully used to any extent in practice and it is indeed doubted that they could be for several reasons. In the first place, because of the blockage of the pupil and the risk of prolapse it is necessary to make one or more holes (iridectomies) within the iris to allow the fluids to circulate within the anterior chamber. Thus, it is doubted that the iris could provide sufficient mechanical support to retain the lenses in position, especially having regard to the weight of the lenses which must be of sufficient thickness to permit anchoring of the support wires. Furthermore, the torque which would be applied to the iris, in particular when the iris is closed, would be more than could be withstood over any sensible length of time. The present invention is therefore exclusively concerned with anterior chamber implants of the type in which the haptic rests on the iris and is retained in position by the edge where the cornea meets the iris.

Such anterior chamber implants were at one point made exclusively of glass, in particular by pioneers in this field such as Strampelli, Baron and Dannheim, who had appreciated the advantages of being able to sterilise the implant by autoclaving. Dannheim, in particular, persevered and inserted approximately thirty six autoclavable implants, the last being in 1958. The work on anterior chamber implants capable of being autoclaved and which were primarily made of glass was however abandoned because of their weight and also because on one or two occasions fractures and later complications occurred, the complications being uveitis, glaucoma and hyphema, which are problems familiar in the present day context in association with injection moulded polymethylmethacrylate anterior chamber implants.

The present day polymethylmethacrylate implants, notably the implants invented by the present applicant and sold under the trade designation Choyce Mark VIII and Choyce Mark IX, do, as earilier stated, enjoy a considerable success but they nevertheless have certain disadvantages of their own, namely:

1. The implants are difficult to manufacture to the necessary high standards, their manufacture requiring a large number of extremely skilled technicians in order to impart a proper finish to the edges and the surfaces of the implants and to ensure the necessary optical quality of the optic itself;

2. The finished product can be damaged very easily, both before it leaves the factory any by the surgeon and his assistants in the operating room;

3. The choice of size of anterior chamber implant remains and will continue to remain a difficult problem to resolve pre-operatively. Only in the operating room can one be absolutely certain as to the best length for the particular recipient's eye. This means that even a skilled operator every so often selects an implant which is either too long or too short. The choice of an incorrect implant involves wastage because although implants may be returned to the manufacturer, it is normally found that they cannot be brought back to the necessary high quality finish to justify re-sterilisation and re-shipping back to the operating surgeon;

4. The best method of sterilisation of polymethylmethacrylate implants is the subject of controversy. The caustic soda method is still used by a major manufacturer in the United Kingdom and when correctly carried out has proved to be perfectly satisfactory. However, this method has come under informed criticism from professional micro-biologists and other scientists connected with the F.D.A. in the United States and the Department of Health and Social Security in the United Kingdom. Thus, this method is still on probation and is not unconditionally accepted. The other method which is widely practiced is the use of ethylene oxide (ETO). There are numerous reports of sterile hypopyons following the use of AC implants sterilised with ETO. Implants sterilised in this manner can be used satisfactorily if thoroughly washed in normal saline before implanatation. However, even with this precaution taken it has been found in practice that the central endothelial cell count in patients is significantly lower than when the wet sterilisation method is employed. In particular, with wet sterilisation the endothelial cell count suffered a loss of 31% in Mark VIII implants before 1975, the loss having been reduced to 23% for current Mark VIII implants and only 17% for current Mark IX implants. This is to be contrasted with Perspex CQ implants sterilised in ETO which, in the present day, cause a loss of 34% in the endothelial cell count and, worst of all, injection moulded anterior chamber implants sterilised in ETO where the loss is as high as 47%. The reason for the relatively high loss in endothelial cell count in Mark VIII implants used before 1975 is that the anterior chamber implant was not routinely re-inflated with air before the introduction of the implant. It seems clear from the foregoing that no method of sterilising nonautoclavable implants has yet proved 100% satisfactory.

5. The end result of all the difficulties in the manufacture and sterilisation, and the ease of degradation of Perspex CQ (Registered Trade Mark) polymethylmethacrylate implants has caused them to be very expensive. Typically, such implants cost in excess of $200 each, making them far too expensive outside the richer industrial nations. Yet the advantages of pseudophakic surgery are clearly apparent to the poorer countries of the world, who are not lacking skilled eye surgeons.

It is therefore seen that despite the obvious desirability of an autoclavable implant no satisfactory such implant has been proposed since the advent of anterior chamber implants.

It is accordingly a primary object of the invention to provide an anterior chamber implant which is capable of being stably retained in the anterior chamber of the eye and which is capable of being sterilized in an autoclave.

In accordance with the present invention, there is provided in an anterior chamber implant comprising an optic to act as an artificial lens and a haptic to support the optic within the anterior chamber at a distance from the iris to avoid blockage of the pupil, the haptic including feet lying in a plane parallel to and spaced from the optic to rest on the anterior surface of the iris in use and being so shaped as to minimise obstruction to circulation of fluids within the anterior chamber of the eye, the improvement wherein the optic is made of glass and the haptic is separately formed from a material capable of being autoclaved and clinically inert to the fluids in the anterior chamber of the eye, the haptic being formed with a lens mount portion for receiving and supporting the lens and inclined intermediate portion extending between the lens mount portion and the feet.

In one embodiment of the invention, the haptic is made of titanium. The use of titanium offers several advantages in the particular context of the anterior chamber implant. Titanium being one of the lighter metals enables the implant to have a relatively small weight in aqueous. The weight is not as small as the corresponding weight of a polymethylmethacrylate implant, but has been found experimentally not to prove a significant hindrance.

The rigidity of titanium allows extensive fenestration of the haptic, thus reducing the obstruction to circulation of aqueous humor within the anterior chamber and thereby reducing the risk of prolapse. The strength also contributes to the reduction of the weight of the implant inasmuch as less material is required to achieve the required rigidity.

A still further advantage is provided if the implant is extensively fenestrated since this makes the implant relatively flexible while being sufficiently strong to hold the lens in place. The flexibility is of considerable value in the insertion of the lens and also serves to maintain the optic stably in place.

Although amongst the metals titanium is preferred, the invention in its broadest aspect is not limited to the use of titanium, it being possible to use gold, tantalum of platinum, though the density of these elements does not render them particularly suitable.

In a second embodiment of the invention, the haptic is made of a high temperature plastics material which is inert and the latter may, if necessary, be reinforced with glass or carbon fibres.

One suitable plastics material is a polyethersulphone (P.E.S.) thermoplastic material available in the United Kingdom from I.C.I. under the trade designation "Victrex". This plastics material is capable of being injection moulded, but is also capable of withstanding the conditions in an autoclave for considerable periods of time. The material may either be injection moulded, vacuum formed or machined into the required shape of the haptic.

Whereas when titanium is used as the material for the haptic, it is preferred to resort to a bonding resin such as an epoxy resin to secure the optic within the haptic, the use of Victrex offers the advantage that a weld may be achieved by locally dissolving the plastics material in a suitable solvent such as chloroform or N, methyl-2-pyrrolidone (N.M.P.).

Preferably, a solution of Victrex in equal parts by volume of N.M.P. and dichloromethane may be used to bond the lens in position. Such a solution can be prepared by dissolving Victrex powder in N.M.P. by stirring the powder into N.M.P. at 20° C. followed by the addition of dichloromethane to form a stable solution.

In a further alternative, the lens may be positioned in a mould and the haptic injection moulded around it, thereby avoiding the need to mount the lens in a separately formed haptic.

The invention will now be described further, with reference to the accompanying drawings, in which.

Figure 1:
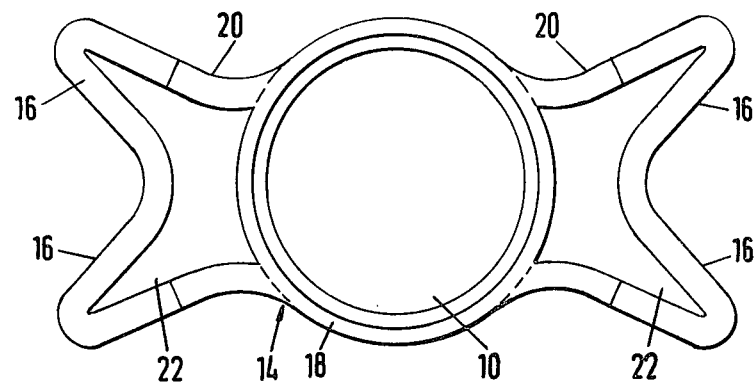
FIG. 1 is a plan view of an anterior chamber implant constructed in accordance with the invention.

In the drawings, an anterior chamber implant is shown, the general shape of which is similar to the known Choyce Mark IX implant as described, for example, in co-pending patent application No. 53425/77. The implant is formed of an optic 10 in the form of a glass plano-convex lens, the posterior surface 12 of the glass being curved. The optic 10 is mounted in a haptic 14 which comprises two sets of flat feet 16 lying in the same plane as one another which are connected to an annular setting 18 for the optic 10 by means of a pair of inclined sections 20, each of which is provided with a fenestration 22. The setting 18 is shown as an annulus having a shoulder 26 on its posterior surface in which sits the plano-convex optic 10. Claws may be formed by punching the metal surrounding the shoulder 26 in order to retain the lens in place, but alternatively use may be made of an epoxy resin glue.

The feet 16 are preferably as wide as the outer diameter of the annular setting 18 and determine the size of the incision required to insert the implant. The haptic is waisted between the feet and the optic in order to reduce the mass of the implant and to improve the circulation of the fluid in the anterior chamber. The fenestrations 22 enhance the circulation further. Preferred dimensions of a 5 mm titanium haptic implant are given in FIG. 3 by way of non-limiting example. It is however envisaged to manufacture implants having an overall width less than 5 mm.

The maximum width of the implant is conveniently 5 mm or less. In order to improve the aperture of the lens it is possible for the lens not to be totally circular, thereby providing a larger area for light to enter the eye without nevertheless increasing the overall width of the implant.

The haptic is conveniently formed of a metal which does not react with the fluid in the anterior chamber. A noble metal such as gold or platinum may be used, but as both of these metals are relatively dense it is preferable, with a view to reducing the weight of the implant, to employ a lighter metal such as titanium or a titanium alloy. A further advantage of titanium resides in the fact that a colour may be imparted to its surface by anodisation, enabling the colour of the haptic to be matched to that of the iris. The metal is also relatively cheap, permitting the cost of the implant to be reduced significantly. The haptic may also be mass produced by stamping from titanium strip, by electro-erosion forming or by chemical etching, helping to reduce the cost of the implant still further.

A feature of the titanium haptic which has been noted experimentally is the absence of what is termed "lenticular" or "pseudophakic" deposits on the anterior surface of the optic portion of the pseudophakos which are common with Perspex CQ implants and which would normally be present during early post-operative stages. These deposits resulted in fogged vision for some time after the insertion of a polymethylmethacrylate anterior chamber implant and their absence is in line with observations made by Barasch on his own glass optic iris plane lens implants.

A clear advantage resulting from the use of titanium is the robustness of the implant which, if now found to be of the wrong length, can simply go back into storage for re-sterilisation. Handling at the time of initial surgery is unlikely to damage the implant or affect its suitability for re-use and sterilisation presents no problem. This, too, is a contributing factor in the reduction in the cost.

Figure 2:
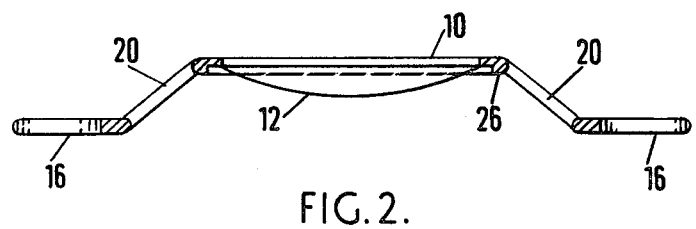
FIG. 2 is a vertical section through the implant shown in FIG. 1.
Figure 3:
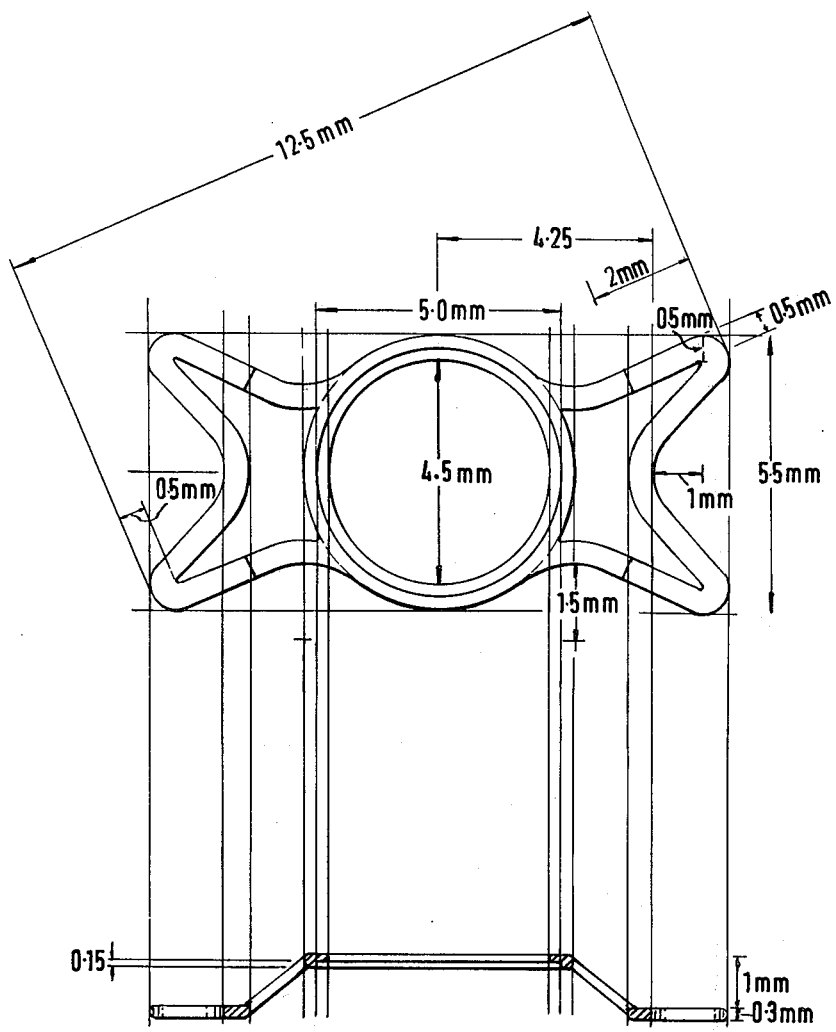
FIG. 3 shows FIGS. 1 and 2 with the addition of suitable dimensions for the haptic when manufactured from titanium.

An alternative embodiment of the invention may have the general appearance of the embodiment described with reference to FIGS. 1, 2 and 3, but the haptic may instead be formed of a polyethersulphone (P.E.S.) thermoplastic material such as sold by I.C.I. under the trade name "VICTREX". This material is available in several grades, some of which are reinforced with glass fibres. The relative density of this plastic, depending on the grade used, is between 1.37 and 1.6 and as result, the weight of the haptic in aqueous is almost negligible. As a consequence, it is possible to use a greater thickness for the haptic than the dimensions given in the drawing for a titanium haptic.

Amongst the important advantages of this P.E.S. thermoplastic material are the fact that it can be autoclaved for very long periods of time and that it can be formed by standard injection moulding techniques using elevated temperatures. Consequently, the haptic may be moulded in large quantities inexpensively and with very high yields.

In order to mount the glass optic within the haptic after it has been injection moulded, it is possible to use a solvent to dissolve the resin locally allowing it to reset after the optic has been placed in position. Suitable solvents are available for this thermoplastics resin with a very wide range of boiling points. Amongst the substances in which Victrex is known to dissolve are the following:
Dichloromethane;
Chloroform;
1,2,Dichloroethane;
1,1,2,2,Tetrachloroethane;
Dimethylformamide (DMF);
Dimethylsulphoxide (DMSO);
N,methyl-2-pyrrolidone (NMP);
Nitrobenzene;
Pyridine;
Aniline;
Dimethylphthalate;
Butyrolactone;
Cyclopentanone.

Conveniently, a formulation may be prepared to be used as a solvent adhesive to secure the optic in position. Such a formulation may be formed by adding Victrex powder slowly to NMP at 20° C. stirring the solution until all the powder has dissolved and then adding Dichloromethane in an amount equal in volume to the NMP. Other suitable preparations are described in application notes available from I.C.I., the manufacturers.

An alternative method for securing the optic to the haptic when the latter is moulded of a thermoplastics material is to position the optic in the mould during injection moulding and to mould the haptic in situ about the optic.

In its normal form, Victrex is a transparent thermoplastics material slighly amber in colour. If it is desired to match the colour of the haptic to that of the iris, it is possible to modify the colour of the thermoplastics material by the addition of suitable pigments or dyes.

I claim:

1. In an anterior chamber implant comprising an optic to act as an artificial lens and a haptic to support the optic within the anterior chamber at a distance from the iris to avoid blockage of the pupil, the haptic including feet lying in a plane parallel to and spaced from the optic to rest on the anterior surface of the iris in use and being so shaped as to minimize obstruction to circulation of fluids within the anterior chamber of the eye, the improvement wherein the optic is made of glass and the haptic is separately formed from a high temperature thermoplastic material comprising a polyethersulphone capable of being autoclaved and clinically inert to the fluids in the anterior chamber of the eye, the haptic being formed with a lens mount portion for receiving and supporting the lens and inclined intermediate portion extending between the lens mount portion and the feet, and wherein the optic is secured to the haptic by the use of a solvent adhesive.

* * * * *